United States Patent
Thuring et al.

(10) Patent No.: US 9,139,523 B2
(45) Date of Patent: Sep. 22, 2015

(54) 5-HT2B RECEPTOR ANTAGONISTS

(71) Applicant: Janssen Pharmaceutica, NV, Beerse (BE)

(72) Inventors: Johannes Wilhelmus John F. Thuring, Antwerpen (BE); Luc August Laurentius Ver Donck, Kasterlee (BE)

(73) Assignee: Janssen Pharmaceutica, NV, Beerse (BE)

( * ) Notice: Subject to any disclaimer, the term of this patent is extended or adjusted under 35 U.S.C. 154(b) by 0 days.

(21) Appl. No.: 14/196,502

(22) Filed: Mar. 4, 2014

(65) Prior Publication Data

US 2014/0187585 A1 Jul. 3, 2014

Related U.S. Application Data

(62) Division of application No. 13/779,962, filed as application No. PCT/EP2011/064906 on Aug. 30, 2011, now Pat. No. 8,703,958.

(30) Foreign Application Priority Data

Sep. 1, 2010 (EP) .................................... 10174880

(51) Int. Cl.
*A61K 31/445* (2006.01)
*C07D 211/58* (2006.01)
*A61K 31/4468* (2006.01)

(52) U.S. Cl.
CPC .......... *C07D 211/58* (2013.01); *A61K 31/4468* (2013.01)

(58) Field of Classification Search
CPC ..................................................... C07D 211/22
USPC ........................................................... 514/317
See application file for complete search history.

(56) References Cited

U.S. PATENT DOCUMENTS

2014/0187585 A1  7/2014  Thuring et al.

FOREIGN PATENT DOCUMENTS

| EP | 0076530 B1 | 12/1985 |
|---|---|---|
| WO | 0193849 A2 | 12/2001 |
| WO | 2007071965 A2 | 6/2007 |
| WO | 2008139152 A1 | 11/2008 |

OTHER PUBLICATIONS

G. Poissonnet et al, The Emergence of Selective 5-HT2B Antagonists Structures, Activities and Potential Therapeutic Applications, Mini-Reviews in Medicinal Chemistry, Mar. 1, 2004, pp. 325-330, vol. 4 No. 3.
S. Collin et al, Moecular structure of two gastrokinetic compounds, cisapride and R53757: comparison with dopaminergic D2 antagonists, Journal of Molecular Structure, Dec. 1, 1989, pp. 159-175, vol. 214.
R.H.P. Porter, et al., Functional characterization of agonists at recombinant human 5-HT2A, 5-HT2B and 5-HT2C receptors in CHO-K1 cells, British Journal of Pharmacology, (1999), pp. 13-20, vol. 128.
International Search Report and Written Opinion, PCT/EP2011/064906, dated Oct. 19, 2011.

*Primary Examiner* — John Mabry

(57) ABSTRACT

The present invention relates to novel fluorinated piperidine derivatives having antagonistic activity at the 5-$HT_{2B}$ receptor, pharmaceutical compositions comprising these compounds and their use as a medicine.

1 Claim, No Drawings

5-HT2B RECEPTOR ANTAGONISTS

CROSS REFERENCE TO RELATED APPLICATIONS

The present application is a divisional application of U.S. application Ser. No. 13/779,962, filed on Feb. 28, 2013 which is a national stage application of Patent Application No. PCT/EP2011/064906, filed on Aug. 30, 2011 which in turn claims the benefit of EPO Patent Application No. 10174880.4 filed Sep. 1, 2010. The complete disclosures of the aforementioned related patent applications are hereby incorporated herein by reference in its entirety.

FIELD OF THE INVENTION

The present invention relates to novel fluorinated piperidine derivatives having antagonistic activity at the 5-$HT_{2B}$ receptor, pharmaceutical compositions comprising these compounds and their use as a medicine.

BACKGROUND OF THE INVENTION

Cisapride is a serotonin 5-$HT_4$ receptor agonist useful as a gastroprokinetic drug. It interacts significantly with several other receptors such as 5-$HT_{2A}$ and 5-$HT_{2C}$; $D_{2L}$; 5-$HT_{3A/B}$; $Alpha_{1A}$, $Alpha_{2A}$, $Alpha_{2B}$ and $Alpha_{2C}$. It was withdrawn from some markets in 2000 due to reports of sudden cardiac arrhythmias. At the origin of this side effect is drug-induced QT prolongation by blockade of the hERG potassium channel (human ether-a-go-go related gene). One of the known pharmacophores of a hERG channel blocker comprises a hydrophilic and a hydrophobic moiety linked by a middle part having a basic nitrogen atom. At physiological pH, the basic nitrogen is protonated and is involved in cation-π interaction with Tyr 652 residues within the hERG channel pore. In order to lower the pKa value of piperidine nitrogen atom, and thereby reduce the likelihood of blockade of the hERG channel, derivatives of cisapride were prepared wherein 3-methoxy-piperidine was replaced by 3-fluoropiperidine and 3,3-difluoropiperidine.

SUMMARY OF THE INVENTION

The present invention concerns a compound of formula (I)

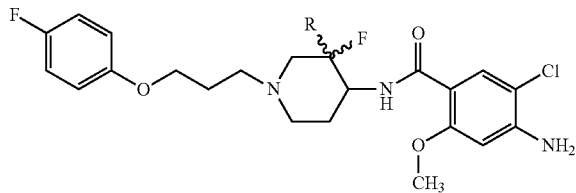

or a stereochemically isomeric form thereof, wherein
R is hydrogen or fluoro, or
an addition salt or a solvate thereof Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the 5-$HT_{2B}$ receptor, comprising administering to a subject in need thereof a therapeutically effective amount of any of the compounds or pharmaceutical compositions described above.

Further exemplifying the invention are methods of inhibiting the 5-$HT_{2B}$ receptor, comprising administering to a subject in need thereof a therapeutically effective amount of any of the compounds or pharmaceutical compositions described above.

An example of the invention is a method of treating a disorder selected from the group consisting of pulmonary arterial hypertension, pulmonary fibrosis, irritable bowel syndrome, cardiovascular disorders such as chronic heart disease, congestive heart failure and hypertension, comprising administering to a subject in need thereof, a therapeutically effective amount of any of the compounds or pharmaceutical compositions described above.

Another example of the invention is any of the compounds described above for use in treating pulmonary arterial hypertension, pulmonary fibrosis, irritable bowel syndrome, cardiovascular disorders such as chronic heart disease, congestive heart failure and hypertension, in a subject in need thereof.

DETAILED DESCRIPTION OF THE INVENTION

The present invention is directed to compounds of formula (I) as defined hereinbefore, and pharmaceutically acceptable salts thereof. The compounds of formula (I) are selective antagonists at the 5-$HT_{2B}$ receptor.

In an embodiment of the present invention, R is fluoro and the compound is a racemic mixture or an addition salt or a solvate thereof.

In another embodiment of the present invention, R is fluoro and the compound has an optical rotation $[\alpha]=+14.1°$ (c=0.3, MeOH, λ=598 nm; 20° C.), or an addition salt or a solvate thereof.

In another embodiment of the present invention, R is fluoro and the compound has an optical rotation $[\alpha]=-14.4°$ (c=0.3, MeOH, λ=598 nm; 20° C.), or an addition salt or a solvate thereof.

In another embodiment of the present invention, R is hydrogen and the substituents in position 3 and 4 of the piperidine moiety have a cis orientation, or an addition salt or a solvate thereof.

In another embodiment of the present invention, R is hydrogen, the substituents in position 3 and 4 of the piperidine moiety have a cis orientation and the compound has an optical rotation $[\alpha]=+39.8°$ (c=0.2, MeOH, λ=598 nm; 20° C.), or an addition salt or a solvate thereof.

In another embodiment of the present invention, R is hydrogen, the substituents in position 3 and 4 of the piperidine moiety have a cis orientation and the compound has an optical rotation $[\alpha]=-45.5°$ (c=0.2, MeOH, λ=598 nm; 20° C.), or an addition salt or a solvate thereof.

In another embodiment of the present invention, R is hydrogen and the substituents in position 3 and 4 of the piperidine moiety have a trans orientation, or an addition salt or a solvate thereof.

In another embodiment of the present invention, R is hydrogen, the substituents in position 3 and 4 of the piperidine moiety have a trans orientation and the compound has an optical rotation $[\alpha]=+19.2°$ (c=0.4, MeOH, λ=598 nm; 20° C.), or an addition salt or a solvate thereof.

In another embodiment of the present invention, R is hydrogen, the substituents in position 3 and 4 of the piperidine moiety have a trans orientation and the compound has an optical rotation [α]=−22.8° (c=0.3, MeOH, λ=598 nm; 20° C.), or an addition salt or a solvate thereof.

As anticipated, the fluorinated cisapride derivatives are significantly less potent hERG channel blockers than cisapride and thus much less likely to cause drug-induced QT prolongation. Unexpectedly though, the receptor affinities change in various ways so as to yield compounds with a more selective profile. Affinities for $5\text{-}HT_{2A}$ and $D_{2L}$ receptors diminish significantly, and for $5\text{-}HT_{3A/B}$, $5\text{-}HT_{4B}$, $Alpha_{1A}$, $Alpha_{2A}$, $Alpha_{2B}$ and $Alpha_{2C}$ receptors they show a trend to a reduction. The only exception is the affinity for the $5\text{-}HT_{2B}$ receptor which increases significantly.

$5\text{-}HT_{2B}$ receptor antagonists are indicated for the treatment or the prevention of pulmonary arterial hypertension, pulmonary fibrosis or irritable bowel syndrome. Pulmonary arterial hypertension may be idiopathic, familial, or associated with other diseases such as HIV infection, or use of certain drugs. It may also be associated with heart or lung diseases such as chronic obstructive pulmonary disease (COPD), interstitial lung disease or chronic exposure to high altitude. Pulmonary fibrosis is characterized by chronic inflammation and progressive fibrosis of the alveolar walls, with steadily progressing dyspnea, resulting finally in death from oxygen lack or right heart failure. Irritable bowel syndrome is a chronic noninflammatory disease characterized by abdominal pain, altered bowel habits consisting of diarrhea or constipation or both, and no pathological change. It is a common disorder with a psychophysiological basis. The $5\text{-}HT_{2B}$ receptor antagonists may also be used to treat cardiovascular disorders such as chronic heart disease, congestive heart failure and hypertension.

Definitions

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds according to formula (I) and the addition salts, hydrates and solvates thereof may contain one or more centers of chirality and exist as stereoisomeric forms.

The term "stereoisomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloro-acetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, meglumine, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid.

Some of the compounds according to formula (I) may also exist in their tautomeric form. Such forms although not explicitly indicated in the above formula are intended to be included within the scope of the present invention.

Pharmaceutical Compositions

The present invention also provides compositions for preventing or treating diseases in which inhibition of pulmonary arterial hypertension or pulmonary fibrosis is beneficial.

Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as inhalation or insufflation. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, suppositories, wafers, injectable solutions or suspensions, powders for inhalation, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

'DCM' means dichloromethane, 'EtOAc' means ethylacetate, "AcOH" means acetic acid, "MeOH" means methanol, "rac" means racemic, "Et$_2$O" means diethylether, "DMAP" means dimethylaminopyridine, "DMSO" means dimethylsulfoxide, "hex" means hexanes and "TFA" means trifluoroacetic acid, DEA means diethylamine.

Example 1

Synthesis of trans-4-amino-5-chloro-N-{3-fluoro-1-[3-(4-fluorophenoxy)-propyl]-piperidin-4-yl}-2-methoxybenzamide 7

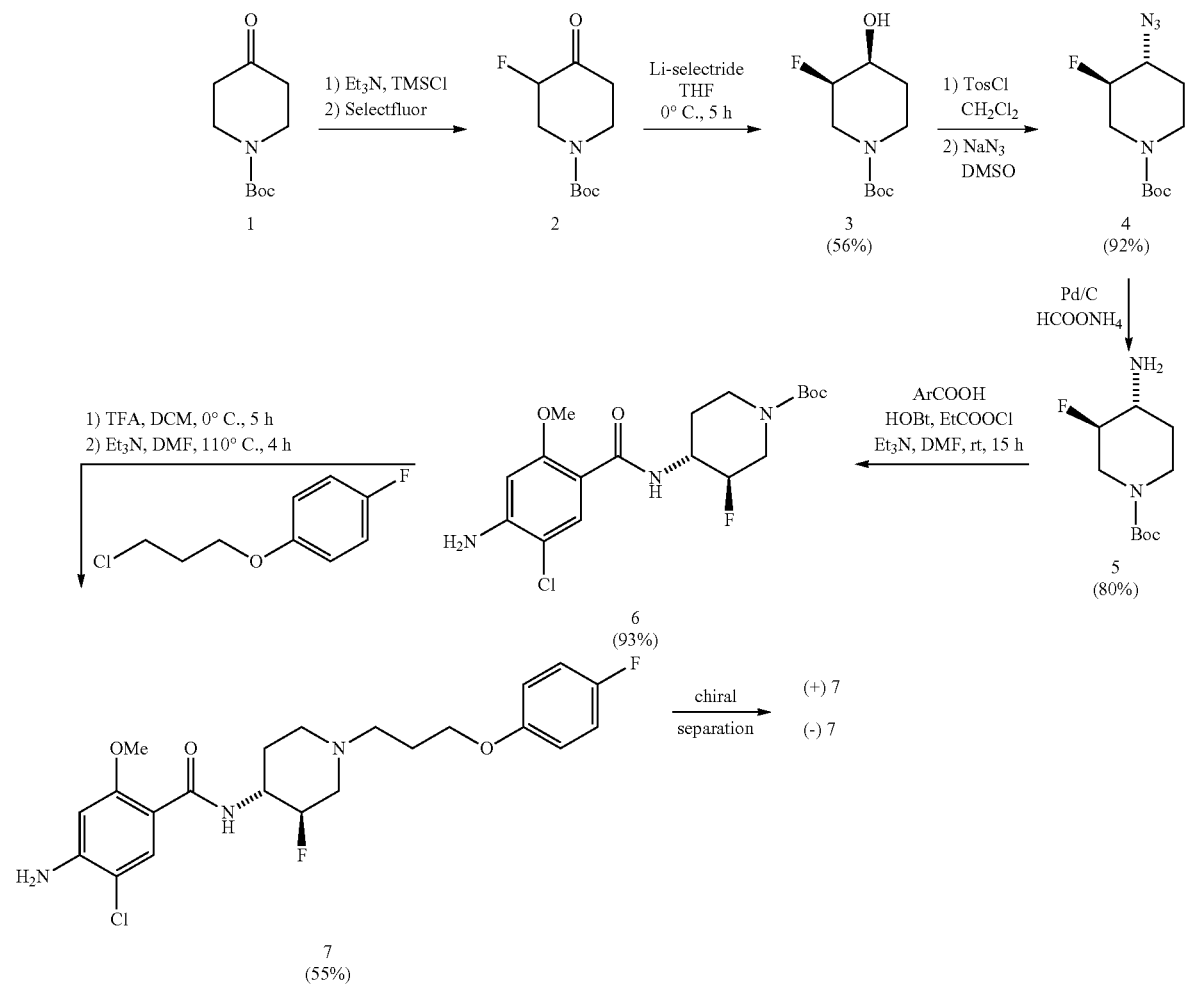

The following examples are intended to illustrate but not to limit the scope of the present invention.

EXPERIMENTAL PART

Synthetic Examples

Hereinafter, the term 'm.p.' means melting point, 'THF' means tetrahydrofuran, 'DMF' means dimethylformamide, Synthesis of cis-1-Boc-3-fluoro-4-hydroxypiperidine 3

To a solution of 0.5 g (2.30 mmol) of N-Boc-3-fluoro-4-piperidinone 2 (J. Med. Chem. 1999, 42, 2087-2104) in 10 mL of dry THF was added dropwise 2.8 mL (2.76 mmol) of a 1M solution of Li-selectride in THF under N$_2$-atmosphere at 0° C. The solution was stirred at 0° C. for 4 h, then 10 mL of NaOH 2M was added at 0° C. and the mixture was stirred overnight at rt. The reaction mixture was extracted with Et$_2$O, dried over MgSO$_4$, filtered and evaporated under reduced pressure. The crude mixture was subjected to flash silicagel chromatography (hex/EtOAc/Et$_3$N 1:1:0.1) to yield 0.27 g (56%) of pure cis-1-Boc-3-fluoro-4-hydroxypiperidine 3 as a colorless oil which solidified upon standing at −20° C. (freezer). Mp 48° C. $^1$H NMR (300 MHz, CDCl$_3$): δ 1.46 (9H, s, 3×CH$_3$), 1.67-1.91 (2H, m, CH$_2$), 2.40-2.65 (1H, m, OH), 2.92-3.35 (2H, m, CH$_2$CH$_a$H$_b$N and CH$_a$H$_b$CHF), 3.55-3.94 (3H, m, CH$_2$CH$_a$H$_b$N and CHOH and CH$_a$H$_b$CHF), 4.52 (1H, dm, J=48.4 Hz, CHF). $^{19}$F NMR (282 MHz, CDCl$_3$): δ −201.9 and −203.1 (1F, 2×m). $^{13}$C NMR (75 MHz, CDCl$_3$): δ 28.4 (3×), 29.2, 40.4, 44.8, 68.0 (d, J=17.3 Hz), 80.2, 88.6 (d, J=177.7 Hz), 155.1. IR (KBr): ν 3413, 1674, 1429, 1167 cm$^{-1}$. GC-MS (EI): m/z (%): 219 (M$^+$, 4), 164 (46), 146 (50), 57 (C$_4$H$_9$$^+$, 100).

Synthesis of trans-4-azido-1-Boc-3-fluoropiperidine 4

To a solution of 0.60 g (2.74 mmol) of cis-1-Boc-3-fluoro-4-hydroxypiperidine 3 in 15 mL DCM was added 0.42 g (4.11 mmol) of triethylamine and 37 mg (0.3 mmol) of 4-(N,N-dimethylamino)pyridine (DMAP) at rt. Then a solution of 0.57 g (3.01 mmol) of p-toluenesulfonyl chloride in 2 mL of DCM was added under a dry atmosphere (CaCl$_2$-tube) at rt. After stirring for 15 h at rt, the solution was poured in brine (20 mL) and extracted with DCM (3×25 mL). After drying over MgSO$_4$, filtration and evaporation of the solvent, the crude mixture was used as such in the next step without further purification. The obtained tosylate was dissolved in 5 mL of dry DMSO and 0.36 g (5.48 mmol) of NaN$_3$ was added. The mixture was stirred under N$_2$-atmosphere at 90° C. for 15 h. After cooling, the mixture was poured in brine (10 mL) and extracted with EtOAc. The combined extract were washed with brine, dried over MgSO$_4$, filtered and evaporated in vacuo. trans-4-Azido-1-Boc-3-fluoropiperidine 4 was obtained as a colorless oil in 92% yield from 4-hydroxypiperidine 3 and was sufficiently pure for further use. $^1$H NMR (CDCl$_3$): δ 1.43 (9H, s); 1.44-1.64 (1H, m); 1.97 (1H, ddd, J=4.3 Hz, 8.4 Hz, 18.0 Hz); 2.99 (1H, ddd, J=3.3 Hz, 10.5 Hz, 13.8 Hz); 3.00-3.15 (2H, m); 3.57-3.68 (1H, m); 3.79 (1H, dt, J=13.8 Hz, J=4.4 Hz); 4.00-4.19 (1H, m); 4.33 (tdd, J=47.9 Hz, J=8.3 Hz, J=4.4 Hz). $^{19}$F NMR (CDCl$_3$): δ −188.1 (1F, d(br), J=47.4 Hz). $^{13}$C NMR (CDCl$_3$): δ 28.3 (4×), 41.2 (br), 45.5 (br), 61.4 (d, J=20.7 Hz), 80.6, 88.9 (d, J=182.3 Hz), 154.4. IR (ATR, cm$^{-1}$): ν=2099, 1693, 1417, 1236, 1161, 1141. MS (ES+) m/z (%): 227 (M+H$^+$, 100).

Synthesis of trans-4-amino-1-Boc-3-fluoropiperidine 5

To a solution of 0.59 g (2.42 mmol) of trans-4-azido-1-Boc-3-fluoropiperidine 4 in 10 mL of MeOH was added 0.61 g (9.67 mmol) of ammonium formate and 0.25 g (0.24 mmol Pd) of 10% Pd on carbon. The reaction mixture was stirred under N$_2$-atmosphere at 50° C. for 5 h. After cooling, the mixture was filtered over diatomaceous earth and evaporated under reduced pressure. The crude mixture was then subjected to flash silicagel chromatography (5% Et$_3$N in EtOAc, short path column) to give 0.42 g (80%) of trans-4-amino-1-Boc-3-fluoropiperidine 5 as an oil. $^1$H NMR (CDCl$_3$): δ 1.39 (9H, s); 1.60 (2H, s(br)); 1.76-1.86 (1H, m); 2.65-2.76 (2H, m); 2.78-2.90 (2H, m); 3.89-3.97 (1H, m); 4.01 (1H, dm, J=48.5 Hz); 4.15-4.30 (1H, m). $^{19}$F NMR (CDCl$_3$): δ −191.0 to −190.3 (1F, m). $^{13}$C NMR (CDCl$_3$): δ 28.4 (3×), 31.8, 41.9 (br), 46.2 (br), 53.5 (d, J=18.5 Hz), 80.3, 93.0 (d, J=177.7 Hz), 154.6. IR (ATR, cm$^{-1}$): ν=1685, 1415, 1244, 1152, 1028. MS (ES+) m/z (%): 204 (M-CH$_3$+H$^+$), 163 (M−3CH$_3$+2H$^+$, 100).

Synthesis of trans-tert-butyl 4-(4-amino-5-chloro-2-methoxybenzoylamino)-3-fluoropiperidine-1-carboxylate 6

To a solution of 0.41 g (2.02 mmol) of 4-amino-5-chloro-2-methoxybenzoic acid in 10 mL of dry DMF was added 0.29 g (2.89 mmol) of triethylamine at room temperature under N$_2$-atmosphere. After stirring for 10 min at rt, a solution of 0.22 g (2.02 mmol) of ethyl chloroformate in 2 mL of DMF was added dropwise at rt and stirring was continued for 30 min, while the temperature was maintained at rt (cooling with waterbath at rt). Then 0.27 g (2.02 mmol) of hydroxybenzotriazole was added as a solid in one portion at rt and the solution was stirred for 30 min. Subsequently, a solution of 0.42 g (1.93 mmol) of amine 5 in 3 mL of DMF was added dropwise at rt and the reaction mixture was stirred overnight at rt. Afterwards, the mixture was poured in 20 mL of brine and extracted with EtOAc (3×25 mL). The combined organic fraction was washed with brine, dried over MgSO$_4$, filtered and evaporated under reduced pressure. The crude mixture was subjected to flash silicagel chromatography (hex/EtOAc/Et$_3$N 1:1:0.1) to yield 0.72 g (93%) of pure trans-tert-butyl 4-(4-amino-5-chloro-2-methoxybenzoylamino)-3-fluoropiperidine-1-carboxylate 6 as a solid. $^1$H NMR (CDCl$_3$): δ 1.47 (9H, s); 2.17-2.28 (1H, m); 2.96-3.19 (2H, m); 3.74 (1H, dm, J=13.7 Hz); 3.90 (3H, s); 3.92-4.40 (3H, m); 4.45 (1H, ddt, J=4.4 Hz, 8.3 Hz, J=48.4 Hz); 6.30 (1H, s); 7.82 (1H, d, J=7.2 Hz); 8.08 (1H, s). $^{19}$F NMR (CDCl$_3$): δ −189.0 (d, J=44.7 Hz). $^{13}$C NMR (CDCl$_3$): δ 28.4 (3×), 29.1 (br), 41.5 (br), 45.6 (br), 50.1 (br), 56.4, 80.4, 88.2 (d, J=182.3 Hz), 97.9, 111.8, 112.1, 133.2, 147.1, 154.7, 157.6; 164.5. IR (ATR, cm$^{-1}$): ν=3478, 3378, 1683, 1619, 1593, 1420, 1247, 1146. MS (ES+) m/z (%): 346/48 (M+H$^+$, 100); 402/404 (M+H$^+$, 60).

Synthesis of trans-4-amino-5-chloro-N-{3-fluoro-1-[3-(4-fluorophenoxy)propyl]-piperidin-4-yl}-2-methoxybenzamide 7

To a solution of 0.14 g (0.34 mmol) of tert-butyl 4-(4-amino-5-chloro-2-methoxybenzoylamino)-3-fluoropiperidine-1-carboxylate 6 in 5 mL of DCM was added 0.39 g (3.4 mmol) of trifluoroacetic acid at 0° C. under dry atmosphere (CaCl$_2$-tube). After stirring for 5 h at 0° C., the mixture was evaporated under reduced pressure. The oily residue was taken up in 10 mL of dry diethyl ether, cooled to 0° C. and the formed crystalline TFA salt was isolated (filter or decant Et$_2$O). After drying and further evaporation the white crystalline TFA-salt of 4-amino-5-chloro-N-(3-fluoropiperidin-4-yl)-2-methoxybenzamide was dissolved in 5 mL of dry DMF. To the solution was added 0.17 g (1.70 mmol) of triethylamine, 55 mg (0.34 mmol) of sodium iodide and then 65 mg (0.34 mmol) of 3-(4-fluorophenoxy)propyl-1-chloride at rt under dry atmosphere. The mixture heated to 110° to 120° C. during 4 h. After cooling, the mixture was diluted with 25 mL of EtOAc, poured in brine (25 mL) and extracted with EtOAc (3×25 mL). The combined organic phase was washed with brine, dried over MgSO4, filtered and evaporated under reduced pressure. The crude mixture was subjected to gradient flash silicagel chromatography (EtOAc/hex/Et3N3: 2:0.1 to 1% Et3N in EtOAc) to give 85 mg (55%) of trans-4-amino-5-chloro-N-{3-fluoro-1-[3-(4-fluorophenoxy)propyl]piperidin-4-yl}-2-methoxybenzamide 7 as a pale yellow solid. Mp 125° C. Optional recrystallization from EtOAc/EtOH. $^1$H NMR (CDCl$_3$): δ 1.46-1.59 (1H, m); 1.94 (2H, quint, J=6.6 Hz); 2.18-2.34 (3H, m); 2.58 (2H, t, J=6.6 Hz); 2.76 (1H, dm, J=11.6 Hz); 3.13 (1H, td(br), J=4.4 Hz, 9.9 Hz); 3.87 (3H, s); 3.96 (2H, t, J=6.6 Hz); 4.09-4.23 (1H, m); 4.47 (1H, ddt, J=4.4 Hz, J=9.4 Hz, J=49.5 Hz); 4.48 (2H, s(br)); 6.02 (1H, s); 6.79-6.86 (2H, m); 6.92-7.00 (2H, m); 7.79 (1H, d, J=7.7 Hz), 8.09 (1H, s). $^{19}$F NMR (CDCl$_3$): δ −187.6 (d, J=51.3 Hz); −124.0 (tt, J=3.9 Hz, J=9.2 Hz). $^{13}$C NMR (CDCl$_3$): δ 27.0, 29.9 (d, J=6.9 Hz), 51.0 (d, J=18.5 Hz), 51.5, 54.6, 56.2, 56.3 (d, J=24.2 Hz), 66.7, 89.0, 90.2 (d, J=178.8 Hz), 97.9, 111.7, 112.3, 2×115.5 (d, J=8.0 Hz), 2×115.8 (d, J=23.0 Hz), 133.2, 147.0, 155.2, 157.3 (d, J=238.9 Hz), 157.6, 164.6. IR (ATR, cm$^{-1}$): ν=3453, 3370, 3317, 3194, 1631, 1584, 1537, 1508, 1250, 1200. MS (ES+) m/z (%): 454/456 (M+H$^+$, 100).

Chiral separation of trans-4-amino-5-chloro-N-{3-fluoro-1-[3-(4-fluorophenoxy)-propyl]-piperidin-4-yl}-2-methoxybenzamide 7

Compound 7 was resolved into its enantiomers by supercritical fluid chromatography.
Amount: 80 mg (Load: 10 mg/3.00 ml)
Conditions:
Column: OD 20×250 mm (I)
Mobile Phase: 37% MeOH (with 0.2% iPrNH2) hold 9.00 min
Parameters: Flow=50 ml/min
  Column temperature=40° C.
  Nozzle pressure=10 MPa
Injection type: stacked injections (8×)
Collection method: Collection using standard peak detection.
Peak 1 eluted at 5 min 20' and yielded the levorotatory enantiomer (−)-7
[α]=−22.8° (c=0.3, MeOH, λ=598 nm; 20° C.).
Peak 2 eluted at 7 min 30' and yielded the dextrorotatory enantiomer (+)-7
[α]=+19.2° (c=0.4, MeOH, λ=598 nm; 20° C.).

Example 2

Synthesis of cis-4-amino-5-chloro-N-{3-fluoro-1-[3-(4-fluorophenoxy)-propyl]-piperidin-4-yl}-2-methoxybenzamide 12

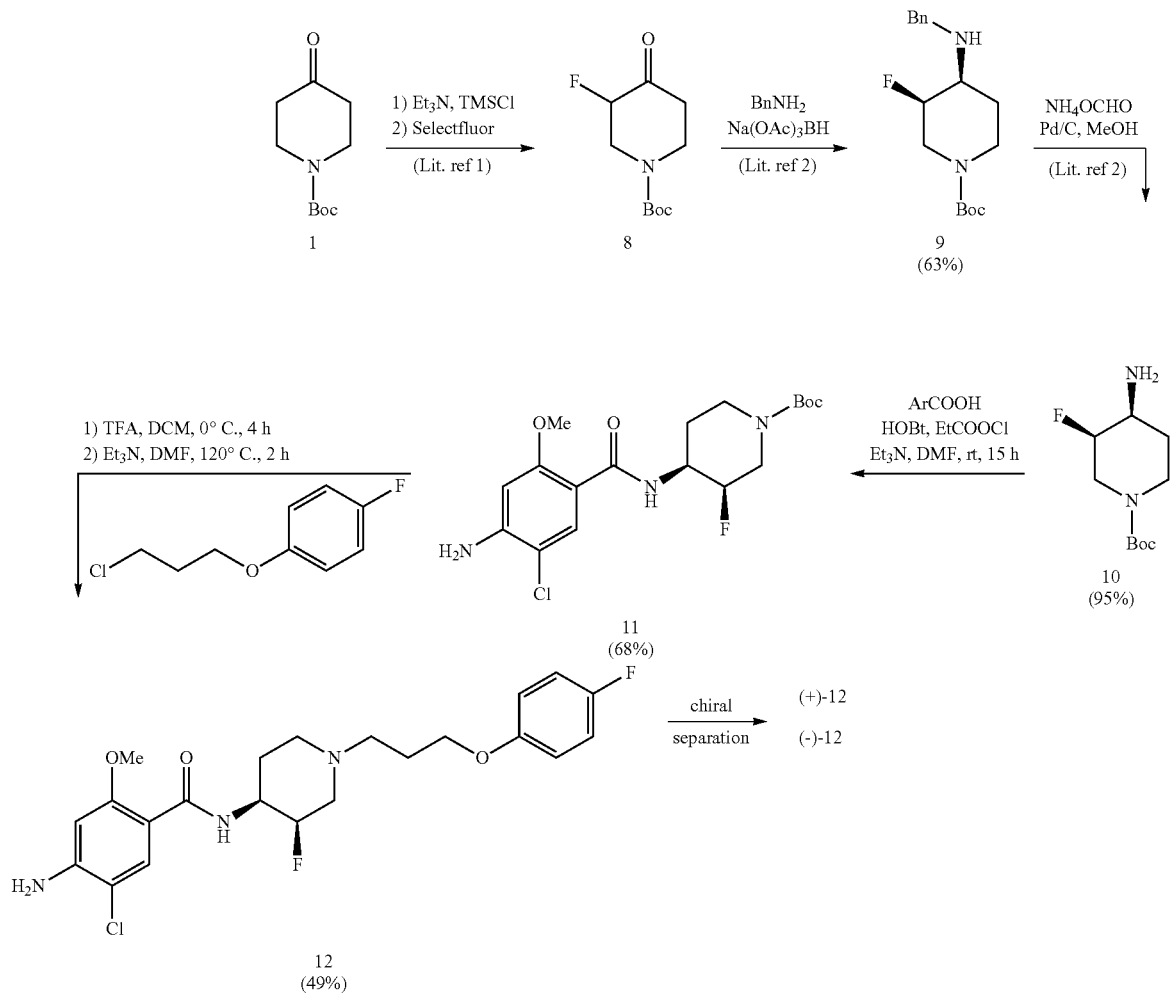

Synthesis of cis-N-(1-Boc-3-fluoropiperidin-4-yl)amine 10

The compound was prepared as disclosed in literature references:
1) *J. Med. Chem.* 1999, 42, 2087-2104, and
2) WO 2007071965.

Synthesis of cis-tert-butyl 4-(4-amino-5-chloro-2-methoxybenzoylamino)-3-fluoro-piperidine-1-carboxylate 11

To a solution of 0.97 g (4.82 mmol) of 4-amino-5-chloro-2-methoxybenzoic acid in 25 mL of dry DMF was added 0.70 g (6.88 mmol) of triethylamine at room temperature under $N_2$-atmosphere. After stirring for 10 min at rt, a solution of 0.52 g (4.82 mmol) of ethyl chloroformate in 1 mL of DMF was added dropwise at rt and stirring was continued for 30 min. Then 0.65 g (4.82 mmol) of hydroxybenzotriazole was added as a solid in one portion at rt and the solution was stirred for 30 min. Subsequently, a solution of 1.0 g (4.59 mmol) of amine 10 in 3 mL of DMF was added dropwise at rt and the reaction mixture was stirred overnight at rt. Afterwards, the mixture was poured in 100 mL of brine and extracted with EtOAc (4×30 mL). The combined organic fraction was washed with brine, dried over $MgSO_4$, filtered and evaporated under reduced pressure. The crude mixture was subjected to flash silicagel chromatography (hex/EtOAc/$Et_3N$ 1:1:0.1; Rf=0.01) to yield 1.25 g (68%) of pure tert-butyl 4-(4-amino-5-chloro-2-methoxybenzoylamino)-3-fluoropiperidine-1-carboxylate 11 as a solid. Mp 198-199° C. $^1H$ NMR ($CDCl_3$): δ 1.35 (9H, s); 1.44-1.77 (2H, m); 2.77-2.98 (1H, m); 3.81 (3H, s); 4.04-4.32 (4H, m); 4.42 (2H, s(br)); 4.65 (1H, d, J=48.9 Hz); 6.23 (1H, s); 7.95 (1H, s(br)); 8.01 (1H, s). $^{19}F$ NMR ($CDCl_3$): δ −203.5 to −204.5 (1F, m). $^{13}C$ NMR ($CDCl_3$): δ 26.6, 28.5 (3×), 42.3 (br), 46.5 (br), 48.6 (d, J=17.3 Hz), 52.2, 80.1, 87.9 (d, J=176.5 Hz), 97.9, 111.6, 112.0, 133.1, 147.1, 155.2, 157.7, 164.0. IR (ATR, cm$^{-1}$): ν=3470, 3393, 3310, 1697, 1637, 1612, 1534, 1420. MS (ES+) m/z (%): 402/404 (M+H$^+$, 100).

Synthesis of cis-4-amino-5-chloro-N-{3-fluoro-1-[3-(4-fluorophenoxy)propyl]-piperidin-4-yl}-2-methoxybenzamide 12

To a solution of 1.00 g (2.49 mmol) of tert-butyl 4-(4-amino-5-chloro-2-methoxybenzoylamino)-3-fluoropiperidine-1-carboxylate 11 in 10 mL of DCM was added 2.83 g (24.9 mmol) of trifluoroacetic acid at 0° C. under dry atmosphere ($CaCl_2$-tube). After stirring for 4 h at 0° C., the mixture was evaporated under reduced pressure. The oily residue was taken up in 25 mL of dry diethyl ether, cooled to 0° C. and the formed crystalline TFA salt was isolated (filter or decant $Et_2O$). After drying and further evaporation in vacuo 0.78 g of the TFA-salt of 4-amino-5-chloro-N-(3-fluoropiperidin-4-yl)-2-methoxybenzamide was obtained as a white solid. To a solution of 0.78 g of the obtained salt in 10 mL of DMF was added 1.26 g (12.45 mmol) of triethyl amine, 0.37 g (2.49 mmol) of sodium iodide and then 0.47 g (2.49 mmol) of 3-(4-fluorophenoxy)propyl-1-chloride at rt under dry atmosphere. The mixture heated to 120° C. for 2 h. After cooling, the mixture was diluted with 25 mL of EtOAc, poured in brine (25 mL) and extracted with EtOAc (3×25 mL). The combined organic phase was washed with brine, dried over $MgSO_4$, filtered and evaporated under reduced pressure. The crude mixture was subjected to gradient flash silicagel chromatography (EtOAc/hex/$Et_3N$ 3:1:0.1 to 1% $Et_3N$ in EtOAc) to give 49% of 4-amino-5-chloro-N-{3-fluoro-1-[3-(4-fluorophenoxy)propyl]piperidin-4-yl}-2-methoxybenzamide 12 as a pale yellow solid. Mp 137° C. Optional recrystallization from EtOAc/EtOH. $^1H$ NMR ($CDCl_3$): δ 1.83-1.92 (2H, m); 1.94 (2H, quint, J=6.6 Hz); 2.10-2.35 (2H, m); 2.47-2.61 (2H, m); 2.94 (1H, d(br), J=11.6 Hz); 3.24 (1H, t(br), J=11.3 Hz); 3.85 (3H, s); 3.95 (2H, t, J=6.6 Hz); 4.08-4.27 (1H, m); 4.41 (2H, s(br)); 4.73 (1H, d(br), J=49.6 Hz); 6.26 (1H, s), 6.76-6.84 (2H, m); 6.89-6.97 (2H, m); 8.03 (1H, s(br)); 8.06 (1H, s). $^{19}F$ NMR ($CDCl_3$): δ −199.3 to −200.0 (1F, m); −124.1 (1F, tt, J=7.9 Hz, J=5.3 Hz). $^{13}C$ NMR ($CDCl_3$): δ 26.9, 27.4, 48.3 (d, J=18.4 Hz), 52.0, 54.7, 56.1 (d, J=18.3 Hz), 56.2, 66.8, 88.8 (d, J=175.3 Hz), 97.9 Hz, 111.6, 112.2, 2×115.6 (d, J=8.0 Hz), 2×115.8 (d, J=23.1 Hz), 133.1, 147.0, 155.2, 157.2 (d, J=237.7 Hz), 157.7, 164.0. IR (ATR, cm$^{-1}$): ν=3477, 3398, 3322, 1636, 1612, 1583, 1537, 1505, 1247, 1209. MS (ES+) m/z (%): 454/456 (M+H$^+$, 100).

Chiral separation of cis-4-amino-5-chloro-N-{3-fluoro-1-[3-(4-fluorophenoxy)propyl]-piperidin-4-yl}-2-methoxybenzamide 12

Compound 12 was resolved into its enantiomers by supercritical fluid chromatography.
Amount: 152 mg (Load: 8.5 mg/1.250 ml)
Conditions:
Column: OJ 20×250 mm (I)
Mobile Phase: 19% MeOH (with 0.2% iPrNH2) hold 14.00 min
Parameters: Flow=50 ml/min
   Column temperature=40° C.
   Nozzle pressure=10 MPa
Injection type: stacked injections (18×)
Collection method: Collection using standard peak detection.
Peak 1 eluted at 10 min 20' and yielded the levorotatory enantiomer (−)-12
[α]=−45.5° (c=0.2, MeOH, λ=598 nm; 20° C.).
Peak 2 eluted at 11 min 40' and yielded the dextrorotatory enantiomer (+)-12
[α]=+39.8° (c=0.2, MeOH, λ=598 nm; 20° C.).

Example 3

Synthesis of 4-amino-5-chloro-N-{3,3-difluoro-1-[3-(4-fluorophenoxy)-propyl]-piperidin-4-yl}-2-methoxybenzamide 17

Synthesis of benzyl-(3,3-difluoro-piperidin-4-yl)amine 14

In a 100 mL flask, 2.00 g (8.0 mmol) of 3,3-difluoro-4,4-dihydroxy-1-trifluoroacetylpiperidine 13 (J. Org Chem. 2010, 75, 929-932) and 2.15 g (20.0 mmol; 2.5 equiv) of benzylamine were dissolved in 50 mL of toluene. The mixture was heated under reflux with a Dean Stark trap during 15 hours. After cooling to room temperature, the solvent was removed in vacuo. The resulting oil was dissolved in 25 mL of absolute methanol and 0.56 g (8.8 mmol; 1.1 equiv) of sodium cyanoborohydride and 0.48 g (8.0 mmol; 1 equiv) of acetic acid were slowly added at room temperature. The solution was stirred during 4 hours at room temperature. After removing the solvent under vacuum, the crude oil was redissolved in 50 mL of dichloromethane and poured in 50 mL of a saturated aqueous $NaHCO_3$ solution and was subsequently extracted with dichloromethane (3×50 mL). The combined organic layers were washed with brine and dried over $MgSO_4$. Filtration of the solids and evaporation of the solvent resulted in a crude oil which was purified via flash chromatography (EtOAc, R$_f$=0.03) yielding 1.32 g (5.8 mmol; 73% yield) of benzyl-(3,3-difluoro-piperidin-4-yl)amine 14 as a yellow oil.

$^1$H NMR (CDCl$_3$): δ 1.51 (1H, q, J=11.8 Hz, CH$_a$H$_b$); 1.69 (1H, s(broad), NH); 1.94 (1H, d, J=11.8 Hz, CH$_a$H$_b$); 2.58 (1H, t, J=12.8 Hz, NCH$_a$H$_b$); 2.74 (1H, dd, J=25.3 Hz, 14.3 Hz, NCH$_a$H$_b$CF$_2$); 2.86-2.97 (1H, m, NCH); 3.02 (1H, d, J=12.8 Hz, NCH$_a$H$_b$); 3.22 (1H, dt, J=14.3 Hz, 9.4 Hz, NCH$_a$H$_b$CF$_2$); 3.91 (1H, d, J=14.9 Hz, CH$_a$H$_b$Ph); 3.96 (1H, d, 14.9 Hz, CH$_a$H$_b$Ph); 7.22-7.38 (5H, m, 5×CH$_{ar}$). $^{19}$F NMR (CDCl$_3$): δ −109.0 (1F, d, J=234.1 Hz); −120.4 (1F, d(broad), J=234.1 Hz). $^{13}$C NMR (CDCl$_3$): δ 31.9 (CH$_2$); 43.3 (NCH$_2$); 50.5 (t, J=27.1 Hz, NCH$_2$CF$_2$); 51.5 (NCH$_2$Ph); 57.1 (t, J=20.8 Hz, NCH); 120.9 (t, J=247.5 Hz, CF$_2$); 126.9 (CH$_{ar}$); 127.9 (2×CH$_{ar}$); 128.3 (2×CH$_{ar}$); 140.1 (C$_{ar}$). IR (ATR, cm$^{-1}$): ν=3324 (NH); 3028; 2930; 2859; 1495; 1453; 1317; 1274; 1181; 1130; 1106; 1072; 983; 912; 855; 740; 699. MS (ES+) m/z (%): 227 (M+H$^+$, 100).

Synthesis of benzyl-{3,3-difluoro-1-[3-(4-fluoro-phenoxy)propyl]piperidin-4-yl}amine In a 100 mL flask, a mixture of 1.22 g (5.4 mmol) of benzyl-(3,3-difluoro-piperidin-4-yl)amine 14, 0.81 g (5.4 mmol; 1 equiv) of sodium iodide, 2.73 g (27.0 mmol; 5 equiv) of triethylamine and 1.05 g (5.4 mmol; 1 equiv) of 1-(3-chloropropoxy)-4-fluorobenzene in 70 mL was stirred at 120° C. during 30 hours. Another portion of 2.73 g (27.0 mmol; 5 equiv) of triethylamine was added and the mixture stirred at 120° C. during 16 hours. Then 1.05 g (5.4 mmol; 1 equiv) of 1-(3-chloropropoxy)-4-fluorobenzene was added and the mixture was stirred at 120° C. during 54 hours until the reaction was completed. The solvent was removed under vacuum and the crude oil was redissolved in 100 mL of EtOAc and washed with brine and dried over MgSO$_4$. Filtration of the solids and evaporation of the solvent resulted in a crude oil which was purified via flash chromatography (hexane/EtOAc 1:1, R$_f$=0.19-0.38) yielding 1.00 g (2.6 mmol; 49% yield) of benzyl-{3,3-difluoro-1-[3-(4-fluoro-phenoxy)propyl]piperidin-4-yl}amine 15 as a brown oil.

$^1$H NMR (CDCl$_3$): δ 1.48-1.62 (1H, m, CH$_a$H$_b$); 1.58 (1H, s(broad), NH); 1.80-1.92 (1H, m, CH$_a$H$_b$); 1.86 (2H, quintet, J=6.9 Hz, CH$_2$); 2.09 (1H, t, J=10.7 Hz, NCH$_a$H$_b$); 2.26 (1H, ddd, J=23.8 Hz, 12.3 Hz, 3.4 Hz, NCH$_a$H$_b$CF$_2$); 2.41-2.57 (2H, m, NCH$_2$); 2.68-2.82 (2H, m, NCH and NCH$_a$H$_b$); 2.99 (1H, td, J=11.3 Hz, 8.8 Hz, NCH$_a$H$_b$CF$_2$); 3.84 (1H, d, J=14.0 Hz, CH$_a$H$_b$Ph); 3.89 (2H, t, J=6.9 Hz, OCH$_2$); 3.91 (1H, d, 14.0 Hz, CH$_a$H$_b$Ph); 6.74 (2H, dd, J=9.4 Hz, 4.4 Hz, 2×CH$_{ar}$); 6.87 (2H, t, J=9.4 Hz, 2×CH$_{ar}$); 7.14-7.30 (5H, m, 5×CH$_{ar}$). $^{19}$F NMR (CDCl$_3$): δ −104.9 (1F, d, J=225.6 Hz, CF$_a$F$_b$); −116.9 (1F, d(broad), J=225.6 Hz, CF$_a$F$_b$); −124.0 (1F, tt, J=7.9 Hz, 4.0 Hz, C$_{ar}$F). $^{13}$C NMR (CDCl$_3$): δ 26.7 (CH$_{2, alkyl}$); 29.2 (d, J=5.8 Hz, CH$_2$); 50.8 (NCH$_2$); 51.5 (NCH$_2$Ph); 53.9 (NCH$_{2, alkyl}$); 57.0 (t, J=20.8 Hz, NCH); 57.2 (t, J=27.7 Hz, NCH$_2$CF$_2$); 66.4 (OCH$_2$); 115.4 (d, J=8.1 Hz, 2×CH$_{ar}$); 115.7 (d, J=23.1 Hz, 2×CH$_{ar}$); 120.9 (t, J=245.2 Hz, CF$_2$); 127.0 (CH$_{ar}$); 128.0 (2×CH$_{ar}$); 128.5 (2×CH$_{ar}$); 140.2 (C$_{ar}$); 155.0 (d, J=2.3 Hz, OC$_{ar}$); 157.1 (d, J=238.8 Hz, C$_{ar}$F). IR (ATR, cm$^{-1}$): ν=3334 (NH); 3062; 3028; 2953; 2823; 1682; 1602; 1505; 1470; 1454; 1388; 1346; 1292; 1247; 1205; 1152; 1118; 1097; 1064; 1028; 987; 912; 828; 736; 699. MS (ES+) m/z (%): 379 (M+H$^+$, 100).

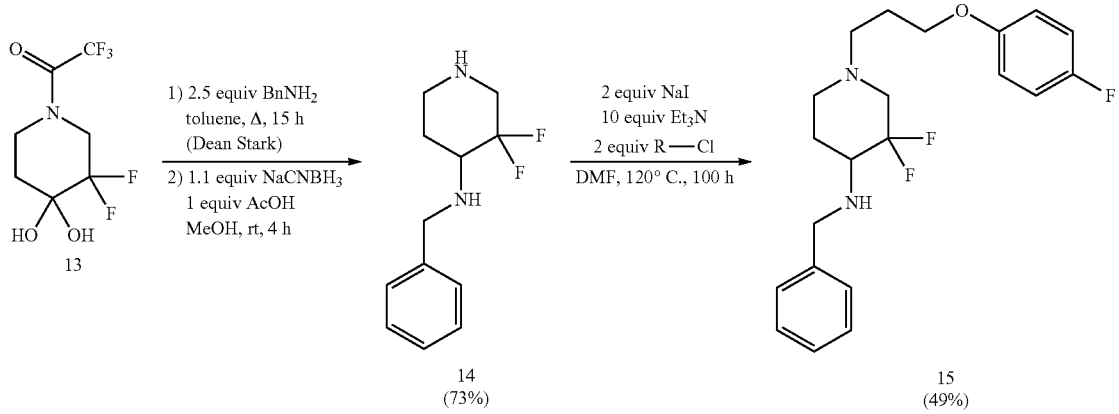

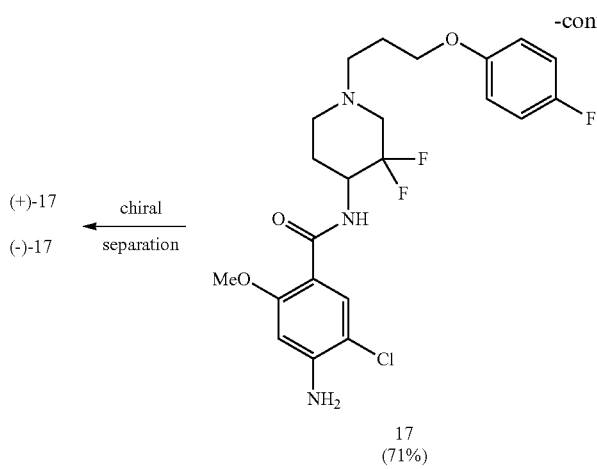
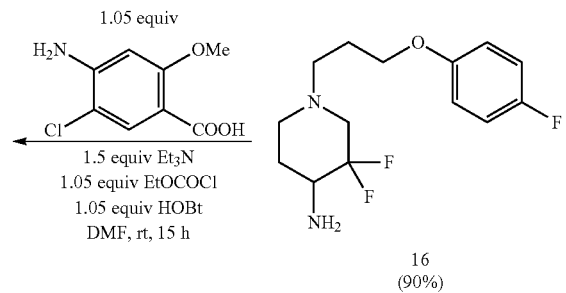

Synthesis of 3,3-difluoro-1-[3-(4-fluorophenoxy)propyl]piperidin-4-amine 16

In a dry pressure vessel, 0.83 g (2.2 mmol) of benzyl-{3,3-difluoro-1-[3-(4-fluoro-phenoxy)propyl]piperidin-4-yl}amine 15 was dissolved in 10 mL of methanol. After adding 0.33 g (40 wt %) of Pd/C (10%) at 0° C., the mixture was stirred during 15 hours at room temperature under hydrogen pressure of 480 kPa. The mixture was filtered over diatomaceous earth. The solvent was evaporated in vacuo to yield 0.57 g (2.0 mmol; 90% yield) of 3,3-difluoro-1-[3-(4-fluorophenoxy)propyl]piperidin-4-amine 16 as a yellow oil.

$^1$H NMR (CDCl$_3$): δ 1.54 (1H, dddd, J=24.5 Hz, 11.3 Hz, 3.7 Hz, 1.7 Hz, CH$_a$H$_b$); 1.80-1.99 (1H, m, CH$_a$H$_b$); 1.86 (2H, quintet, J=6.7 Hz, CH$_2$); 2.11 (1H, t, J=11.6 Hz, NCH$_a$H$_b$); 2.21 (1H, ddd, J=26.4 Hz, 12.1 Hz, 2.2 Hz, NCH$_a$H$_b$CF$_2$); 1.42 (2H, s(broad), NH$_2$); 2.44-2.61 (2H, m, NCH$_2$); 2.76-2.92 (2H, m, NCH and NCH$_a$H$_b$); 3.00-3.13 (1H, m, NCH$_a$H$_b$CF$_2$); 3.90 (2H, t, J=6.7 Hz, OCH$_2$); 6.75 (2H, dd, J=9.4 Hz, 4.4 Hz, 2×CH$_{ar}$); 6.88 (2H, t, J=9.4 Hz, 2×CH$_{ar}$). $^{19}$F NMR (CDCl$_3$): δ -109.6 (1F, d, J=239.4 Hz, CF$_a$F$_b$); -120.5 (1F, d(broad), J=239.4 Hz, CF$_a$F$_b$); -124.0 (1F, tt, J=7.9 Hz, 4.0 Hz, C$_{ar}$F). $^{13}$C NMR (CDCl$_3$): δ 26.8 (CH$_{2,\ alkyl}$); 30.6 (d, J=6.9 Hz, CH$_2$); 51.4 (NCH$_2$); 52.8 (t, J=22.5 Hz, NCH); 53.9 (NCH$_{2,\ alkyl}$); 57.0 (dd, J=29.4 Hz, 24.8 Hz, NCH$_2$CF$_2$); 66.4 (OCH$_2$); 115.4 (d, J=6.9 Hz, 2×CH$_{ar}$); 115.7 (d, J=21.9 Hz, 2×CH$_{ar}$); 119.6 (dd, J=245.8 Hz, 241.1 Hz, CF$_2$); 155.0 (OC$_{ar}$); 157.2 (d, J=237.7 Hz, C$_{ar}$F). IR (ATR, cm$^{-1}$): ν=3384; 2952; 2821; 1601; 1505; 1470; 1390; 1348; 1294; 1247; 1204; 1146; 1078; 915; 828; 757; 735. MS (ES+) m/z (%): 289 (M+H$^+$, 100).

Synthesis of 4-amino-5-chloro-N-{3,3-difluoro-1-[3-(4-fluorophenoxy)propyl]-piperidin-4-yl}-2-methoxybenzamide 17

In a dry 50 mL flask, 0.44 g (2.2 mmol; 1.1 equiv) of 4-amino-5-chloro-2-methoxybenzoic acid and 0.30 g (3 mmol; 1.5 equiv) of triethylamine were dissolved in 25 mL of dimethylformamide and stirred during 10 minutes at room temperature. Then the mixture was cooled to 0° C. and 0.24 g (2.2 mmol; 1.1 equiv) of ethyl chloroformate was added and stirred during 30 minutes at room temperature. Then 0.29 g (2.2 mmol; 1.1 equiv) of 1-hydroxybenzotriazole was added and stirred during 30 minutes at room temperature. Then 0.57 g of 3,3-difluoro-1-[3-(4-fluorophenoxy)propyl]piperidin-4-amine 16 was added and the mixture was stirred at room temperature during 15 hours. After evaporation of the solvent in vacuo, the crude oil was redissolved in EtOAc and poured in 50 mL of brine and extracted with EtOAc (4×50 mL). The organic phases were washed with brine and dried over MgSO$_4$. After filtration of the solids and evaporation of the solvent under vacuum, the crude oil was purified via flash chromatography (hexane/EtOAc 3:7, R$_f$=0.35) yielding 0.66 g (1.4 mmol; 71% yield) of pure 4-amino-5-chloro-N-{3,3-difluoro-1-[3-(4-fluorophenoxy)propyl]piperidin-4-yl}-2-methoxybenzamide 17 as white crystals. M.p.=125.8° C. (hexane/EtOH 1:1).

$^1$H NMR (CDCl$_3$): δ 1.70 (1H, ddd, J=24.8 Hz, 12.7 Hz, 3.9 Hz, CH$_a$H$_b$); 1.93 (2H, quintet, J=6.6 Hz, CH$_2$); 2.01-2.12 (1H, m, CH$_a$H$_b$); 2.21 (1H, t, J=11.8 Hz, NCH$_a$H$_b$); 2.34 (1H, ddd, J=28.8 Hz, 11.3 Hz, 1.7 Hz, NCH$_a$H$_b$CF$_2$); 2.50-2.69 (2H, m, NCH$_2$); 2.92 (1H, d, J=11.8 Hz, NCH$_a$H$_b$); 3.19 (1H, td, J=11.3 Hz, 4.4 Hz, NCH$_a$H$_b$CF$_2$); 3.86 (3H, s, OCH$_3$); 3.96 (2H, t, J=6.6 Hz, OCH$_2$); 4.43 (3H, s(broad), NCH and NH$_2$); 6.26 (1H, s, CH$_{ar}$); 6.81 (2H, dd, J=8.8 Hz, 4.4 Hz, 2×CH$_{ar}$); 6.94 (2H, t, J=8.8 Hz, 2×CH$_{ar}$); 8.03 (1H, s(broad), NH); 8.06 (1H, s, CH$_{ar}$). $^{19}$F NMR (CDCl$_3$): δ -107.6 (1F, d, J=240.7 Hz, CF$_a$F$_b$); -116.9 (1F, d(broad), J=240.7 Hz, CF$_a$F$_b$); -124.0 (1F, tt, J=7.9 Hz, 4.0 Hz, C$_{ar}$F). $^{13}$C NMR (CDCl$_3$): δ 26.8 (CH$_{2,\ alkyl}$); 29.6 (d, J=5.8 Hz, CH$_2$); 50.2 (t, J=19.6 Hz, NCH); 51.5 (NCH$_2$); 53.9 (NCH$_{2,\ alkyl}$); 56.2 (OCH$_3$); 58.0 (dd, J=29.4 Hz, 23.7 Hz, NCH$_2$CF$_2$); 66.3 (OCH$_2$); 97.8 (CH$_{ar}$); 111.6 (C$_{ar}$CO); 111.9 (C$_{ar}$Cl); 115.4 (d, J=8.1 Hz, 2×CH$_{ar}$); 115.7 (d, J=23.1 Hz, 2×CH$_{ar}$); 118.9 (t, J=245.8 Hz, CF$_2$); 133.1 (CH$_{ar}$); 147.1 (C$_{ar}$NH$_2$); 155.0 (d, J=2.3 Hz, OC$_{ar}$); 157.2 (d, J=237.7 Hz, C$_{ar}$F); 157.6 (C$_{ar}$OMe); 164.4 (C=O). IR (ATR, cm$^{-1}$): ν=3480; 3398; 3329; 3194; 2964; 2886; 2818; 1641; 1614; 1584; 1538; 1506; 1462; 1318; 1247; 1208; 1146; 1124; 1074; 1037; 982; 910; 822; 753; 681. MS (ES+) m/z (%): 472/474 (M+H$^+$, 100).

Chiral separation of 4-amino-5-chloro-N-{3,3-difluoro-1-[3-(4-fluorophenoxy)propyl]-piperidin-4-yl}-2-methoxybenzamide 17

170 mg of 17 was resolved into its enantiomers by supercritical fluid chromatography on a Berger Multigram™ SFC (Mettler, Toledo Co., Ltd) with an IC 250 mm*50 mm, 5 mm column.

Mobile phase: supercritical $CO_2$: MeOH with 0.05% DEA=75:25 at 160 ml/min
Column temperature: 38° C.
Nozzle pressure: 30 MPa
Nozzle temperature: 60° C.
Evaporator temperature: 20° C.
Trimmer temperature: 25° C.
Wavelength: 220 nm.
Peak 1 eluted at 7.4 min and yielded the dextrorotatory enantiomer (+)-17
e.e.%=100%; [α]=+14.1° (c=0.3, MeOH, λ=598 nm; 20° C.).
Peak 2 eluted at 8.5 min and yielded the levorotatory enantiomer (−)-17
e.e.%=98.6%; [α]=−14.4° (c=0.3, MeOH, λ=598 nm; 20° C.).

Pharmacological Examples

Example 4

Receptor Binding

Competitive radioligand binding assays were used to determine the affinity of the test compounds for a particular receptor. Various concentrations of the non-labelled test compound were added to the incubation mixture with the membrane fraction, containing the receptor of interest, and a fixed low concentration (nM) of the radioligand. During the incubation the radioligand bound to the receptor, but this was inhibited by the non-labelled test compound in proportion to its binding affinity and concentration.

Cell lines were established that stably express the human variant of the receptor under investigation after transfection with the appropriate cDNA (Table 1). Transfected cells were grown under standard culture conditions, and membrane fractions were obtained upon centrifugation and homogenisation of the cells. Optimal membrane dilutions for binding studies were determined and aliquots were stored at −70° C. until use. In a 96-well plate format, the appropriate radioligand was added to the membrane preparation containing the receptor under investigation. Compound solutions were prepared in DMSO, and diluted 100-fold into the multiwell plate to a final test concentration of $10^{-9}$ to $10^{-5}$ M. After incubation with the test compound, the unbound radioligand was removed by filtration on G/F filters with a Filtermate 96. Microscint™ was added to the washed filter plates and the radioactivity bound to the receptor was measured by liquid scintillation counting in a TopCount (Packard). To measure the Non-Specific Binding (NSB), a high concentration of the non-radiolabeled ligand was added to wells containing the membrane fraction and the radioligand.

TABLE 1

Summary of assay conditions for inhibition of radioligand binding to the receptors evaluated.

| Receptor | Cell line | Radioligand | Conc. (nM) | Kd (nM) |
|---|---|---|---|---|
| $5HT_{1A}$ | HEK293 | 3H-8-OH-DPAT | 0.5 | 0.557 |
| $5HT_{2A}$ | NIH3T3 | 3H-ketanserin | 2 | 0.628 |
| $5HT_{2B}$ | CHO | 3H-5-HT | 4 | 2.312 |
| $5HT_{2C}$ | CHO | 3H-mesulergin | 1 | 1.909 |
| $5HT_{3A/B}$ | HEK293 | 3H-GR65630 | 0.5 | 0.247 |
| $5HT_{4B}$ | HEK293 | 3H-GR113808 | 0.1 | 0.059 |
| $Alpha_{1A}$ | CHO | 3H-prazosin | 0.25 | 0.226 |
| $Alpha_{2A}$ | CHO | 3H-rauwolscine | 1 | 0.485 |
| $Alpha_{2B}$ | CHO | 3H-rauwolscine | 1 | 0.853 |
| $Alpha_{2C}$ | CHO | 3H-rauwolscine | 1 | 0.100 |
| $D_{2L}$ | CHO | 3H-spiperone | 0.2 | 0.239 |
| hERG | HEK293 | 3H-dofetilide | 5 | 3.66 |

The % inhibition of binding of the radioligand to the receptor induced by the test compound was calculated by the formula % Effect=100−[(sample−NSB)/(HC−NSB)*100], where sample=radioactive count in a drug treated well, HC=radioactive count in control wells incubated with radioligand only. Using in house developed software, a best-fit curve was fitted by a minimum sum of squares method to the plot of % inhibition vs. concentration of the test compound. From this, the pIC50 value (inhibitory concentration causing 50% displacement of specific binding) was determined, as well as an estimate of the slope of the plot (Hill coefficient).

TABLE 2

| Co. No. Target | Ref. | (±)-17 | (+)-17 | (−)-17 | (±)-7 | (+)-7 | (−)-7 | (±)-12 | (+)-12 | (−)-12 | trend |
|---|---|---|---|---|---|---|---|---|---|---|---|
| $5HT_{1A}$ | 5.71 | 5.1 | 5.25 | <5 | 5.74 | 6.17 | 5.96 | 5.38 | 6.13 | 5.73 | = |
| $5HT_{2A}$ | 7.84 | 5.71 | 5.59 | 5.76 | 6.95 | 7.15 | 6.12 | 6.44 | 6.49 | 6.31 | ↓ |
| $5HT_{2B}$ | 6.62 | 7.86 | 7.29 | 8.14 | 6.97 | 6.89 | 6.6 | 7.18 | 6.83 | 7.14 | ↑ |
| $5HT_{2C}$ | 5.73 | 5.33 | <5 | 5.18 | 5.74 | 5.91 | 5.43 | 5.36 | 5.3 | 5.18 | = |
| $5HT_{3A/B}$ | 5.94 | <5 | <5 | <5 | <5 | <5 | <5 | 5.17 | <5 | 5.56 | ↘ |
| $5HT_{4B}$ | 6.65 | <5 | <5 | <5 | 6.21 | 6.06 | 6.36 | 6.94 | 6.9 | 6.27 | ↘ |
| $Alpha_{1A}$ | 6.39 | <5 | <5 | 5.11 | <5 | 6.28 | 6.4 | 6.35 | 6.26 | 6.48 | ↘ |
| $Alpha_{2A}$ | 6.05 | <5 | <5 | <5 | 5.44 | <5 | 5.11 | 5.32 | 5 | 5.09 | ↘ |
| $Alpha_{2B}$ | 6.19 | <5 | <5 | <5 | 5.6 | 5.58 | 5.22 | 5.6 | 5.47 | 5.28 | ↘ |
| $Alpha_{2C}$ | 6 | <5 | <5 | <5 | 6.02 | <5 | 5.93 | 5.68 | 5.71 | 5.23 | ↘ |
| $D_{2L}$ | 6.27 | 4.98 | <5 | <5 | 5.34 | 5.56 | 5.10 | 5.33 | 5.32 | 5.32 | ↓ |
| hERG | 7.42 | 5.12 | <5 | <5 | 6.63 | 6.54 | 6.5 | 6.5 | 6.75 | 6.72 | ↓ | pIC$_{50}$ values

The reference compound (Ref.) is cisapride.

Example 5

5-HT$_{2B}$ Antagonism

CHO-K1 (ECACC) cells were stably transfected with human 5-HT$_{2B}$ receptor cDNA subcloned into pCDNA3.1 using the calcium phosphate method. Stably transfected cell lines were selected using G-418, and clonal cell lines were developed by limit dilution. Cell lines were cultured in Dulbecco's modified Eagle Medium (DMEM) containing 10% heat inactivated dialyzed foetal bovine serum (FBS), 1% penicillin-streptomycin, 1% L-glutamine and 1% non-essential amino acids.

Confluent monolayers plated into black 96 well plates with clear bottoms were loaded with 4 µM Fluo-3-AM for 90 min at 37° C. in Hanks balanced salt solution supplemented with 20 mM HEPES and 2.5 mM probenecid. After washing, the test compound was added to the cells and maximal fluorescence in response to 0.1 nM serotonin was recorded using a fluorometric imaging plate reader (FLIPR) to detect changes in intracellular calcium levels.

The maximal fluorescence recorded in the presence of the test compound was expressed as a percent of the maximal fluorescence response to the agonist serotonin (0.1 nM). The $IC_{50}$ value was determined by non-linear regression analysis of the concentration-response curves generated with mean replicate values using Hill equation curve fitting ($Y=D+[(A-D)/(1+(C/C_{50})nH)]$, where Y=specific response, D=minimum specific response (no drugs or serotonin added), A=maximum specific response (0.1 nM serotonin, no drugs), C=concentration of compound, and $C_{50}=IC_{50}$, and nH=slope factor) (SigmaPlot® 4.0, SPSS Inc.). The apparent dissociation constant ($K_B$) was calculated using the modified Cheng Prusoff equation ($K_B=IC_{50}/(1+(A/EC_{50A}))$, where A=concentration of serotonin, and $EC_{50A}=EC_{50}$ value of serotonin in this assay). (Porter et al. (1999), Br. J. Pharmacol., 128: 13-20)

TABLE 3

| 5-HT$_{2B}$ antagonism | | |
|---|---|---|
| Compound | IC$_{50}$ | K$_B$ |
| (±)-7 | 60 nM | 20 nM |
| (±)-12 | 12 nM | 4.2 nM |
| (+)-17 | 33 nM | 11 nM |
| (−)-17 | 1.6 nM | 0.55 nM |

Example 6 hERG-Transfected HEK293 Cells Using a Patch Express Apparatus

Experiments were performed using HEK293 cells stably expressing the hERG potassium channel. Cells were grown at 37° C. and 5% $CO_2$ in culture flasks in MEM Medium supplemented with 10% heat-inactivated fetal bovine serum, 1% L-Glutamine-Penicillin-Streptomycin-solution, 1% non-essential amino acids (100×), 1% sodium pyruvate (100 mM) and 0.8% Geneticin (50 mg/ml). Before use the cells were subcultured in MEM medium in the absence of 5 ml L-Glutamine-Penicillin-Streptomycin. For use in the automated patch-clamp system PatchXpress 7000A (Axon Instruments) cells were harvested to obtain cell suspension of single cells. Extracellular solution contained (mM): 150 NaCl, 4 KCl, 1 $MgCl_2$, 1.8 $CaCl_2$, 10 HEPES, 5 Glucose (pH 7.4 with NaOH). Pipette solution contained (mM): 120 KCl, 10 HEPES, 5 EGTA, 4 ATP-$Mg_2$, 2 $MgCl_2$, 0.5 $CaCl_2$ (pH 7.2 with KOH).

Patch-clamp experiments were performed in the voltage-clamp mode and whole-cell currents were recorded with an automated patch-clamp assay utilizing the PatchXpress 7000A system (Axon Instruments). Current signals were amplified and digitized by a Multiclamp amplifier, stored and analyzed by using the PatchXpress, DataXpress software and Igor 5.0 (Wavemetrics).

The holding potential was −80 mV. The hERG current (K+-selective outward current) was determined as the maximal tail current at −40 mV after a 2 second depolarization to +60 mV. Pulse cycling rate was 15 s. Before each test pulse a short pulse (0.5 s) from the holding potential to −60 mV was given to determine (linear) leak current. After establishing whole-cell configuration and a stability period, the vehicle (aqueous DMSO control) was applied for 5 minutes followed by the test substance by increasing concentrations of $10^{-7}$ M, $3\times10^{-7}$ M and $3\times10^{-6}$ M.

Each concentration of the test substance was applied twice. The effect of each concentration was determined after 5 min as an average current of 3 sequential voltage pulses. To determine the extent of block the residual current was compared with vehicle pre-treatment. Data are expressed as % block at the indicated concentrations in Table 4. The values between brackets refer to % block by the vehicle.

TABLE 4

| | % block of the hERG channel | | |
|---|---|---|---|
| Concentration | 100 nM | 300 nM | 3000 nM |
| Cisapride | 80 (7) | 95 (15) | not tested |
| (±)-7 | 35 (7) | 62 (15) | 94 (21) |
| (±)-12 | 40 (7) | 73 (15) | 96 (21) |
| (±)-17 | 9 (7) | 17 (15) | 58 (21) |
| (+)-17 | 14 (7) | 21 (10) | 52 (11) |
| (−)-17 | 3 (7) | 11 (10) | 47 (11) |

Example 7

Monocrotaline-Induced Pulmonary Arterial Hypertension in the Rat

Compound (−)-17 was tested in monocrotaline-induced pulmonary arterial hypertension in the rat (see e.g., Stenmark et al, 2009, Am J Physiol Lung Cell Mol Physiol 297, L1013-L1032). Measurements included: mean arterial blood pressure and right ventricular pressure in vivo, ratio of right ventricular weight to left ventricular weight plus septum as an index of right ventricular hypertrophy, pulmonary artery acceleration time, and histological assessement of muscularization of pulmonary arteries.

Monocrotaline was dissolved in 1 N HCl and then into distilled water, and pH was adjusted to 7.4 using NaOH. A single dose of 60 mg/kg monocrotaline was administered subcutaneously on day 0 to three groups of male Sprague Dawley rats. The test article Compound (−)-17 was dissolved in 20% hydroxypropyl-beta-cyclodextrin with NaOH, HCl and mannitol in pyrogen-free water and administered orally by gavage (10 ml/kg) once daily from day 1 for 21 days at 10 mg/kg and 50 mg/kg. Plasma concentrations of Compound (−)-17 were measured 2 hours (approximate Cmax after oral dosing in rats) after the final administration on day 21. Corresponding volumes of 20% hydroxypropyl-beta-cyclodextrin vehicle were administered orally according to the same protocol in a third group of animals.

Three-week treatments with Compound (−)-17 at 10 mg p.o. once daily (mean plasma concentration 2 hours post-dosing at day 21~80 ng/ml) and at 50 mg p.o. once daily (mean plasma concentration 1,000 ng/ml) were non-toxic, and had no effect on mean arterial blood pressure (MAP), but reduced right ventricular pressure (RVP), right ventricular hypertrophy (right ventricle/(left ventricle+septum); RV/(LV+S)), and increased pulmonary artery acceleration time (PAAT) (Table 5). The mean wall thickness of small pulmonary arteries was significantly increased by monocrotaline treatment, and this thickening was reduced by a three-week treatment with Compound (−)-17 at 50 mg/kg p.o. (P=0.0539) and at 10 mg p.o. (P<0.005).

TABLE 5

| Treatment | MAP (mmHg) | RVP (mmHg) | RV/(LV + S) | PAAT (ms) |
|---|---|---|---|---|
| Vehicle | 92.53 ± 20.18 | 52.45 ± 9.16 | 0.66 ± 0.16 | 11.63 ± 2.36 |
| Compound (−)-17 10 mg/kg p.o. | 93.7 ± 14.11 | 43.18 ± 7.38 * | 0.46 ± 0.08 * | 15.91 ± 2.76 * |
| Compound (−)-17 50 mg/kg p.o. | 97.58 ± 9.74 | 42.85 ± 11.55* | 0.41 ± 0.08 * | 15.42 ± 2.62 * |

Values are mean ± SD measured at Day 21.
* $p < 0.05$ compared to vehicle

Example 8

Cardiovascular Effects in the Anaesthetized Guinea-Pig

Female guinea-pigs were anesthetized with sodium pentobarbital (66 mg/kg i.p.) followed by a continuous i.v. infusion of 6 mg/h of sodium pentobarbital and prepared for measurements of the surface electrocardiogram (ECG), heart rate and mean arterial blood pressure (see De Clerck et al, Fundam. Clin. Pharm.; 2002; 16: 125-140). Compound (−)-17 was dissolved in 20% hydroxypropyl-cyclodextrin with NaOH, HCl and mannitol in pyrogen-free water and administered intravenously (0.5 ml/kg) in increasing doses (0.16, 0.32, 0.64, 1.25, 2.5 and 5 mg/kg) over a period of 5 min at 15-min intervals. Plasma concentrations of Compound (−)-17 were measured at the end of each infusion. Corresponding volumes of vehicle were administered according to the same protocol in a second group of animals.

Relative to vehicle, Compound (−)-17 at 0.16 up to 5 mg/kg (total dose: 9.87 mg/kg; Cmax: 11,950 ng/ml) had no relevant effect on heart rate, the duration of the PQ, QRS, QT and QTcB intervals, or on ECG morphology in the anesthetized guinea-pig (Table 6). From 2.5 mg/kg onwards (Cmax: 6,325 ng/ml; Table 7), mean arterial blood pressure started to increase (Table 6).

The reference compound dofetilide (0.02 mg/kg i.v. over 1 min), given 15 min after the onset of the last infusion of vehicle, decreased heart rate and prolonged the QT and QTcB intervals.

TABLE 6

Effects of Compound (−)-17 before and at 2, 5 and 15 minutes after onset of each infusion, expressed as percentage changes relative to baseline values on heart rate (HR), mean arterial blood pressure (MBP) and on ECG parameters in anesthesized guinea pigs. Baseline values are presented as actual units.

| | Parameter | | | | | |
|---|---|---|---|---|---|---|
| Baseline | HR b/min 230 | MBP mmHg 33 | PQ ms 63 | QRS ms 31 | QT ms 185 | QTc B ms 361 |
| 0.16 mg/kg @ 2' | −1% | 4% | 0% | −2% | 0% | −1% |
| 0.16 mg/kg @ 5' | 0% | *13%* | 1% | −2% | −1% | −1% |
| 0.16 mg/kg @ 15' | −2% | −3% | 4% | 0% | 1% | 1% |
| 0.32 mg/kg @ 2' | −1% | 6% | 2% | −2% | 0% | 1% |
| 0.32 mg/kg @ 5' | −4% | 2% | 4% | 0% | 3% | 1% |
| 0.32 mg/kg @ 15' | −4% | −3% | 4% | 0% | 4% | 3% |
| 0.64 mg/kg @ 2' | −5% | 6% | 5% | 0% | 7% | 4% |
| 0.64 mg/kg @ 5' | −2% | 13% | 5% | −5% | 5% | 2% |
| 0.64 mg/kg @ 15' | −5% | −5% | 4% | −3% | 8% | 4% |
| 1.25 mg/kg @ 2' | −7% | 4% | 5% | −2% | 8% | 4% |
| 1.25 mg/kg @ 5' | −7% | 15% | 6% | 0% | 6% | 2% |
| 1.25 mg/kg @ 15' | 0% | 9% | 6% | −3% | 2% | 3% |
| 2.5 mg/kg @ 2' | −5% | *17%* | 7% | −3% | 6% | 4% |
| 2.5 mg/kg @ 5' | −6% | 21% | 7% | −3% | 6% | 3% |
| 2.5 mg/kg @ 15' | −4% | 8% | 8% | 0% | 6% | 5% |

TABLE 6-continued

Effects of Compound (−)-17 before and at 2, 5 and 15 minutes after onset of each infusion, expressed as percentage changes relative to baseline values on heart rate (HR), mean arterial blood pressure (MBP) and on ECG parameters in anesthesized guinea pigs. Baseline values are presented as actual units.

| | Parameter | | | | | |
|---|---|---|---|---|---|---|
| Baseline | HR b/min 230 | MBP mmHg 33 | PQ ms 63 | QRS ms 31 | QT ms 185 | QTc B ms 361 |
| 5 mg/kg @ 2' | −3% | *36%* | 6% | −2% | 7% | 5% |
| 5 mg/kg @ 5' | −3% | *34%* | 6% | 0% | 3% | 2% |

Values are median of n = 6. Statistically significant differences ($p < 0.05$) are indicated in bold and italic, and were calculated on the changes from baseline in actual units.

TABLE 7

Median plasma levels of Compound (−)-17 (ng/ml) after administration of increasing intravenous doses of 0.16, 0.32, 0.64, 1.25, 2.5 and 5 mg/kg over periods of 5 minutes at 15-minute intervals (n = 6)

| Dose | 0.16 | 0.32 | 0.64 | 1.25 | 2.5 | 5 |
|---|---|---|---|---|---|---|
| Median | 398 | 873 | 1815 | 3330 | 6325 | 11950 |

Example 9

Bleomycin-Induced Lung Fibrosis in the Mouse (Prophetic

Male C57BL/6 mice are treated intratracheally with bleomycin sulfate (aqueous solution 2.5 U/ml; 2 ml/kg BW) under isoflurane inhalation anesthesia (see e.g., Ishii Y et al, 2006. Am J Respir Crit Care Med. 174(5):550-6). Thereafter Compound (−)-17 is administered once daily for 2 weeks at 10 mg/kg and 50 mg/kg p.o. Post-mortem examination includes gross pathology, lung weights and lung histopathology on Day 15. Histopathological examination of the lungs indicates that bleomycin causes inflammation followed by fibrosis in the lungs in untreated mice.

Example 10

Pharmacokinetic Evaluation in the Mouse

For intravenous (i.v.) administration, Compound (−)-17 was dissolved in saline containing 20% (w/v) hydroxy-propyl-beta-cyclodextrin (HPbCD) at a concentration of 0.25 mg/mL and administered (10 mL/kg) to male CD1 mice (n=3) as a bolus via a tail vein at a dose level of 2.5 mg/kg. For oral (p.o.) administration, Compound (−)-17 was dissolved in water containing 20% (w/v) HPbCD at a concentration of 0.5 mg/mL and administered (20 mL/kg) to male CD1 mice (n=3) via gavage at a dose level of 10 mg/kg. Blood samples were collected via a saphenous vein at serial time points up to 24 h after dosing. Plasma was obtained by centrifugation and stored at −20° C. prior to analysis. Analysis was performed using liquid chromatography (LC) with tandem mass spectrometric detection (MS/MS) in positive ion mode. Compound (−)-17 was eluted from a reversed phase column with a gradient of acetonitrile and water containing 0.1% (v/v) formic acid. At the time of analysis plasma samples (20 uL) were thawed and deprotonated with 200 uL of acetonitrile and centrifuged. Aliquots of the supernatant were injected onto a reversed phase UPLC column and analysed via electrospray Mass Spectrometry. Calibration standards and quality controls, analysed before and after the study samples, were prepared in mouse plasma at the same time as the. The accuracy (intra branch accuracy from independent QC samples) was between 85% and 115% of the nominal value over the entire concentration range. Non-compartmental pharmacokinetic analysis of the plasma concentration-time curves was performed using WinNonLin to provide estimates of the plasma clearance (CLp), volume of distribution at steady-state (Vss), terminal phase elimination half-life (VA) and oral bioavailability (F), the results are summarised in Table 8.

Example 11

Pharmacokinetic Evaluation in the Rat

For intravenous (i.v.) administration, Compound (−)-17 was dissolved in saline containing 20% (w/v) hydroxy-propyl-beta-cyclodextrin (HPbCD) at a concentration of 1 mg/mL and administered (2.5 mL/kg) to male Sprague Dawley rats (n=1) as a bolus via a saphenous vein at a dose level of 2.5 mg/kg. For oral (p.o.) administration, Compound (−)-17 was dissolved in water containing 20% (w/v) HPbCD at a concentration of 1 mg/mL and administered (10 mL/kg) to male Sprague Dawley rats (n=3) via gavage at a dose level of 10 mg/kg. Blood samples were collected via a tail vein at serial time points up to 24 h after dosing. Plasma was obtained by centrifugation and stored at −20° C. prior to analysis. Analysis was performed using liquid chromatography (LC) with tandem mass spectrometric detection (MS/MS) in positive ion mode. Compound (−)-17 was eluted from a reversed phase column with a gradient of acetonitrile and water containing 0.1% (v/v) formic acid. At the time of analysis plasma samples (50 uL) were thawed and deprotonated with at least three volumes of acetonitrile and centrifuged. Aliquots of the supernatant were injected onto a reversed phase UPLC column and analysed via electrospray Mass Spectrometry. Calibration standards and quality controls, analysed before and after the samples, were prepared in rat plasma at the same time as the study samples. The accuracy (intra branch accuracy from independent QC samples) was between 85% and 115% of the nominal value over the entire concentration range. Non-compartmental pharmacokinetic analysis of the plasma concentration-time curves was performed using WinNonLin to provide estimates of the plasma clearance (CLp), volume of distribution at steady-state (Vss), terminal phase elimination half-life (t½) and oral bioavailability (F), the results are summarised in Table 8.

TABLE 8

Non-Compartmental Pharmacokinetic Parameters for Compound (−)-17 obtained in Mouse and Rat Following i.v. and p.o. Administration of Compound (−)-17-AAA (the free base).

| Parameter | Mouse | Rat |
|---|---|---|
| CL (mL/min/kg) | 20 ± 6 | 46 |
| Vss (L/kg) | 1.9 ± 0.6 | 3.1 |
| t½ (h) | 1.4 ± 0.2 | 1.1 |
| Cmax (ng/mL) PO | 1580 ± 165 | 119 ± 37 |
| Tmax (h) PO | 0.5 [0.5-1.0] | 0.5 |
| AUC(0-t) (ng · h/mL) PO | 4443 ± 1093 | 686 ± 254 |
| F (%) | 52 | 19 |

Example 12

Cardio-Hemodynamic, Cardio-Electrophysiological, Electroencephalographic and Pulmonary/Respiratory Effects in Artificially Ventilated, Anesthetized Dogs (Beagles The animals were anesthetized with a mixture of 0.015 mg/kg i.v. scopolamine and 0.075 mg/kg i.v. lofentanil, and relaxed with succinylcholine (5 mg/kg i.v.) followed by a continuous i.v. infusion of 1.5 mg/kg/h of etomidate and small additional doses of fentanyl (0.025 mg/kg i.v.) were given at 60 min intervals. The animals were ventilated and prepared for measurements of the surface ECG, aortic-, pulmonary- and left ventricular blood pressure, carotid blood flow, monophasic action potential, body temperature, blood gasses and EEG (see Van Deuren et al, J Pharmacol Toxicol Methods; 2009; 60: 11-23). Compound (−)-17 was dissolved in 20% hydroxypropyl-cyclodextrin with NaOH, HCl and mannitol in pyrogen-free water and administered intravenously (1 ml/kg) in increasing doses (0.16, 0.32, 0.63, 1.25, 2.5 and 5 mg/kg) over a period of 5 min at 30-min intervals. Plasma concentrations of Compound (−)-17 were measured before and at the end of each infusion. Corresponding volumes of vehicle were administered according to the same protocol in a second group of animals.

Relative to vehicle, Compound (−)-17 at 0.16 up to 5 mg/kg (total dose: 9.86 mg/kg; median Cmax: 20,375 ng/ml) had no relevant effect on heart rate (HR), pulmonary artery pressure, left ventricular end diastolic pressure, cardiac output, stroke volume, pressure rate product, the duration of the PQ and QRS intervals, lung function (dynamic compliance, $C_{dyn}$ and airway resistance, $R_{aw}$), body temperature or on EEG (measured by the Narcotrend®) in the anesthetized dog. From 1.25 mg/kg onwards (Cmax: 5,205 ng/ml), arterial blood pressure, vascular resistance (systemic and common carotid) and Tau (time constant of relaxation) started to increase. Furthermore, at 2.5 mg/kg (Cmax: 9,550 ng/ml) LV $dp/dt_{max}/pd$ started to decrease and at 5 mg/kg (Cmax: 20,375 ng/ml) a minor decrease was noted in the duration of QTc VDW (QT interval corrected for HR) and QTc VcT (QT interval corrected for HR and temperature).

TABLE 9

Effects of Compound (−)-17 before and at 5 and 30 minutes after onset of each infusion, expressed as percentage changes relative to vehicle, on heart rate (HR), mean arterial blood pressure (MBP), systolic (SPP) and diastolic (DPP) pulmonary pressure, left ventricular contractility ($LVdp/dt_{max}$) and ECG parameters (PQ, QRS and QTcV) in anesthetized beagle dogs. Baseline values are presented as actual units.

| | Parameters | | | | | | | |
|---|---|---|---|---|---|---|---|---|
| | HR | MBP | SPP | DPP | $LVdp/dt_{max}$ | PQ ms | QRS | QTcV |
| | | | | Units | | | | |
| Baseline | b/min 64 | mmHg 103 | mmHg 29 | mmHg 12 | mmHg/s 3123 | 97 | ms 46 | ms 294 |
| 0.16 mg/kg @ 5' | −4% | +2% | +2% | +3% | −1% | −1% | +1% | +2% |
| 0.16 mg/kg @ 30' | −5% | +3% | +5% | −3% | +0% | −0% | +2% | +4% |
| 0.32 mg/kg @ 5' | −5% | +5% | +11% | +0% | +0% | −2% | +3% | +2% |
| 0.32 mg/kg @ 30' | +3% | +2% | −3% | −8% | −4% | −2% | +4% | +1% |
| 0.63 mg/kg @ 5' | −0% | +6% | −2% | +0% | −3% | +3% | +4% | +1% |
| 0.63 mg/kg @ 30' | +4% | +2% | −1% | −9% | −2% | −0% | +1% | +4% |
| 1.25 mg/kg @ 5' | −0% | +10% | −1% | −7% | −1% | +2% | +4% | +2% |
| 1.25 mg/kg @ 30' | −3% | +0% | −9% | −12% | −5% | +2% | +2% | +1% |
| 2.5 mg/kg @ 5' | −5% | *+13%* | −1% | +1% | −8% | +6% | +2% | −3% |
| 2.5 mg/kg @ 30' | −4% | +0% | −15% | −24% | +2% | +2% | +3% | −1% |
| 5 mg/kg @ 5' | −15% | *+17%* | −10% | +17% | −11% | +2% | +6% | −3% |
| 5 mg/kg @ 30' | −14% | +0% | −7% | −5% | +2% | +−2% | +3% | −2% |

Values are median of n = 4. Statistically significant differences (p < 0.05) are indicated in bold and italic, and were calculated on the changes from baseline in actual units.

TABLE 10

Median plasma levels of Compound (−)-17 (ng/ml) after administration of increasing intravenous doses of 0.16, 0.32, 0.64, 1.25, 2.5 and 5 mg/kg over periods of 5 minutes at 30-minute intervals (n = 4).

| Dose (mg/kg) | 0.16 | 0.32 | 0.64 | 1.25 | 2.5 | 5 |
|---|---|---|---|---|---|---|
| Median (ng/ml) | 725 | 1420 | 2540 | 5205 | 9550 | 20375 |

The invention claimed is:

1. A method of treating pulmonary arterial hypertension, pulmonary fibrosis or irritable bowel syndrome, the method comprising administering to a subject in need thereof a therapeutically effective amount of a compound of Formula (I)

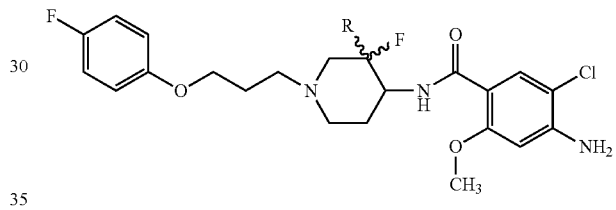

or a stereochemically isomeric form thereof, wherein
R is hydrogen or fluoro, or
an addition salt thereof.

* * * * *